United States Patent
Bädorf et al.

(10) Patent No.: US 6,468,281 B1
(45) Date of Patent: Oct. 22, 2002

(54) INSTRUMENT FOR MANIPULATING COMPONENTS OF JOINT PROSTHESES

(75) Inventors: Dirk Bädorf, Frechen (DE); Hartmut Kälberer, Hochdorf (DE); Hans-Georg Pfaff, Ostfildern (DE); Robert Rack, Plochingen (DE)

(73) Assignees: Ceramtec AG, Plochingen (DE); Innovative Ceramic Engineering, Plochingen (DE)

( * ) Notice: Subject to any disclaimer, the term of this patent is extended or adjusted under 35 U.S.C. 154(b) by 0 days.

(21) Appl. No.: 09/673,541

(22) PCT Filed: Apr. 29, 1999

(86) PCT No.: PCT/EP99/02933

§ 371 (c)(1),
(2), (4) Date: Nov. 20, 2000

(87) PCT Pub. No.: WO99/56677

PCT Pub. Date: Nov. 11, 1999

(30) Foreign Application Priority Data

Apr. 30, 1998 (DE) .......................................... 198 19 193
May 11, 1998 (DE) .......................................... 198 20 721

(51) Int. Cl.⁷ .................................................. A61F 2/34
(52) U.S. Cl. .......................................... 606/91; 606/99
(58) Field of Search ..................... 606/91, 99

(56) References Cited

U.S. PATENT DOCUMENTS

| 5,169,399 A | 12/1992 | Genevieve et al. |
| 5,571,111 A | 11/1996 | Aboczky |

FOREIGN PATENT DOCUMENTS

| DE | 92 90 017.8 | 11/1993 |
| DE | 196 11 249 A | 9/1997 |
| DE | 196 28 193 A | 1/1998 |
| DE | 197 22 923 A | 8/1998 |
| EP | 0 888 759 A | 1/1999 |
| FR | 2 701 206 A | 8/1994 |
| WO | WO 94 21199 A | 9/1994 |

*Primary Examiner*—David Isabella
(74) *Attorney, Agent, or Firm*—Fulbright & Jaworski LLP

(57) ABSTRACT

An instrument for manipulating, detachably holding and placing an insert portion of a joint socket prosthesis into an outer shell of a said prosthesis. The instrument includes a handle and a holding tool. The holding tool includes two or more grasping claws which extend radially from the longitudinal axis of the handle over the insert, and serve to engage the insert to the holding tool. The handle is elongated and slideably positioned within a longitudinal bore or hole in the holding tool and typically includes a plunger. The insert is released when an operator causes the handle to slide within the holding tool towards the insert with sufficient force to disengage the insert from the grasping claws.

9 Claims, 3 Drawing Sheets

INSTRUMENT FOR MANIPULATING COMPONENTS OF JOINT PROSTHESES

The invention relates to an instrument for handling an insert shell and for inserting it into an outer shell of a two-part joint socket prosthesis according to the preamble of the first claim.

Joint prostheses in which one joint partner is constructed as a socket and the other joint partner is constructed as a spherical head which is rotatably mounted in the socket are known in particular from shoulder and hip-joint prostheses. These prostheses are, as a rule, of modular construction. This means, for example, that the joint socket has two parts and comprises an outer shell, which is inserted into the bone, and an insert shell, which is inserted into the outer shell and produces the joint surface, the sliding surface for the other joint partner. The insertion of the sliding shell into the outer shell takes place, as a rule, by means of press fit. For this purpose, it is necessary for the insert shell to be aligned very precisely with respect to the outer shell in order to avoid tilting during insertion. Apart from an imprecise association of the joint surface with respect to the spherical head, damage to the insert shell can occur in the case of a tilted insertion. In particular, insert shells made of ceramic material can break or even shatter.

If the insert shells are inserted by the surgeon by hand, the handling in the area around the operative wound is difficult because of the surgeon's gloves being wet with body fluids and because of the lack of a clear view. For this reason, it is known to provide instruments which improve the handling of insert shells to be inserted. A handling instrument for joint components having joint surfaces is known from German Utility Model DE 297 02 093 U1, which handling instrument has a handle portion and a suction element arranged on the end thereof, which suction element comprises a sealing element contained therein which can be placed in a sealing manner against the joint surface of the joint component and, as a result of this, forms with this joint surface a closed suction chamber, and also a device which lowers the pressure of the suction chamber. This handling instrument is placed with the sealing element on the joint surface of the insert shell to be inserted, the pressure in the suction chamber is lowered and, as a result of this, the insert shell is picked up by suction. After the insertion of the insert shell, the pressure is raised again and the handling instrument is automatically detached from the inserted insert shell.

The known handling instrument, however, offers no certainty that the insert shell can be put on to the outer shell with the required accuracy and that, as a result of this, tilting can be avoided. Apart from this, the known handling devices are long (up to 40 cm). They are therefore unwieldy and are thus lacking in the required sensitivity during the insertion process.

The underlying object of the present invention is to introduce an instrument for handling an insert shell and for inserting it into an outer shell of a two-part joint socket prosthesis, with which instrument a simple positioning and a tilt-free insertion are possible.

The object is achieved with the aid of the characterizing features of the first claim. Advantageous developments of the invention are claimed in the subclaims.

The instrument in accordance with the invention for handling an insert shell and for inserting it into an outer shell of a two-part joint socket prosthesis comprises a handle with a holding tool connected thereto. The holding tool for the insert shell can be handled easily by means of the handle. The holding tool has at least two gripping dogs. These extend substantially radially with respect to the longitudinal axis of the handle. The claws of the gripping dogs rest on the end-face circumferential surface of the insert shell to be inserted.

As a result of the arrangement of the gripping dogs and their claws, the insert shell is held such that it is aligned precisely concentrically with respect to the longitudinal axis of the handle and at right angles to this axis. As a result of this, a precise alignment of the insert shell during insertion is possible for the surgeon. Apart from this, the short structure of the instrument gives the surgeon the required sensitivity during the insertion process.

The claws of the gripping dogs grip around the tapering outer surface of the insert shell by the same length in each case, and to the extent that, on the one hand, reliable holding but also, on the other hand, easy ejection from the claws are possible. The ejection of the insert shell from the gripping dogs of the holding tool takes place by means of a plunger, which is mounted in a sliding manner in a bore which extends concentrically with respect to the longitudinal axis of the handle. When the plunger is slid in the direction of the insert shell, the latter is pushed out of the claws of the gripping dogs and can be pressed into the outer shell of the joint socket prosthesis.

In a development of the invention, the claws of the gripping dogs have end faces which extend at right angles to the longitudinal axis. These end faces are used for placing on the end face of the outer shell. Because the claws on the gripping dogs are all the same length, when all of the dogs are placed on to the end face of the outer shell, the insert shell is positioned precisely for its insertion. This development of the gripping dogs with which, in the difficult surroundings of the operative wound, the surgeon can position the insert shell reliably and precisely for the insertion, is an advantageous aid for the surgeon.

In order that no impairment of the position of the insert shell takes place during the positioning of the instrument with the insert shell on the outer shell, the length of the claws is at least dimensioned in such a way that when they are placed on to the end face of the outer shell, the insert shell held by them still has no clamping contact with the outer shell. In this way, a correction of the positioning is possible at any time. This is ended when all of the dogs rest with their end faces on the end face of the outer shell.

In a further development of the invention, the dogs are made of an elastic material in order that the insert shell which is held can easily be pushed out of the holding tool. A further advantage consists in that insert shells which differ from each other only slightly in terms of their diameters can be held by one and the same holding tool.

In another development of the invention, the claws of the gripping dogs are produced from an elastic material. Particularly in the case of instruments which are used only once, the claws can be constructed in such a way that they even deform permanently when the insert shell is pushed out of the gripping dogs.

In a further advantageous development of the invention, the handle has a recessed grip. This recessed grip renders possible, for example, the clamping of the handle between two parallel fingers, for example the middle finger and the ring finger or the index finger and the middle finger. The recessed grip can be U-shaped, for example, and extend around the entire handle, so that optimal holding of the instrument in the hand of the surgeon is possible in any possible alignment. The pushing-out of the insert shell can then, for example, take place by means of the thumb or the upper hand.

In order that the plunger does not exert a point-focussed load on the insert shell during the ejection of the insert shell from the gripping dogs, it is advantageous if the end thereof has at least one plate with which it is supported in a ring-shaped manner on the insert shell. Such a plate has the advantage that the plunger can be used for insert shells with different joint-surface diameters.

In another development of the invention, the plunger has, on its end, a stamping head which is matched to the joint surface of the insert shell. The stamping head then has the shape of a spherical segment, the radius of which corresponds to the radius of the joint surface. Such a plunger can admittedly be used only for one diameter of an insert shell, but has the advantage that it distributes the force to be applied during insertion over a large surface and evenly on to the insert shell.

As a rule, the pressing of the insert shell into the outer shell is carried out manually by the surgeon. However, for the final fixing, a subsequent blow with a striking tool may be required. In such a case, the instrument in accordance with the invention also offers a possibility of applying such a fixing blow in a targeted manner on to the insert shell. As a result of the precise alignment of the instrument with respect to the outer shell and thus of the insert shell with respect to the outer shell, the forces applied by the blow are introduced into the insert shell evenly and precisely in accordance with their purpose.

The invention is explained in greater detail with the aid of an exemplifying embodiment.

Figure 1:
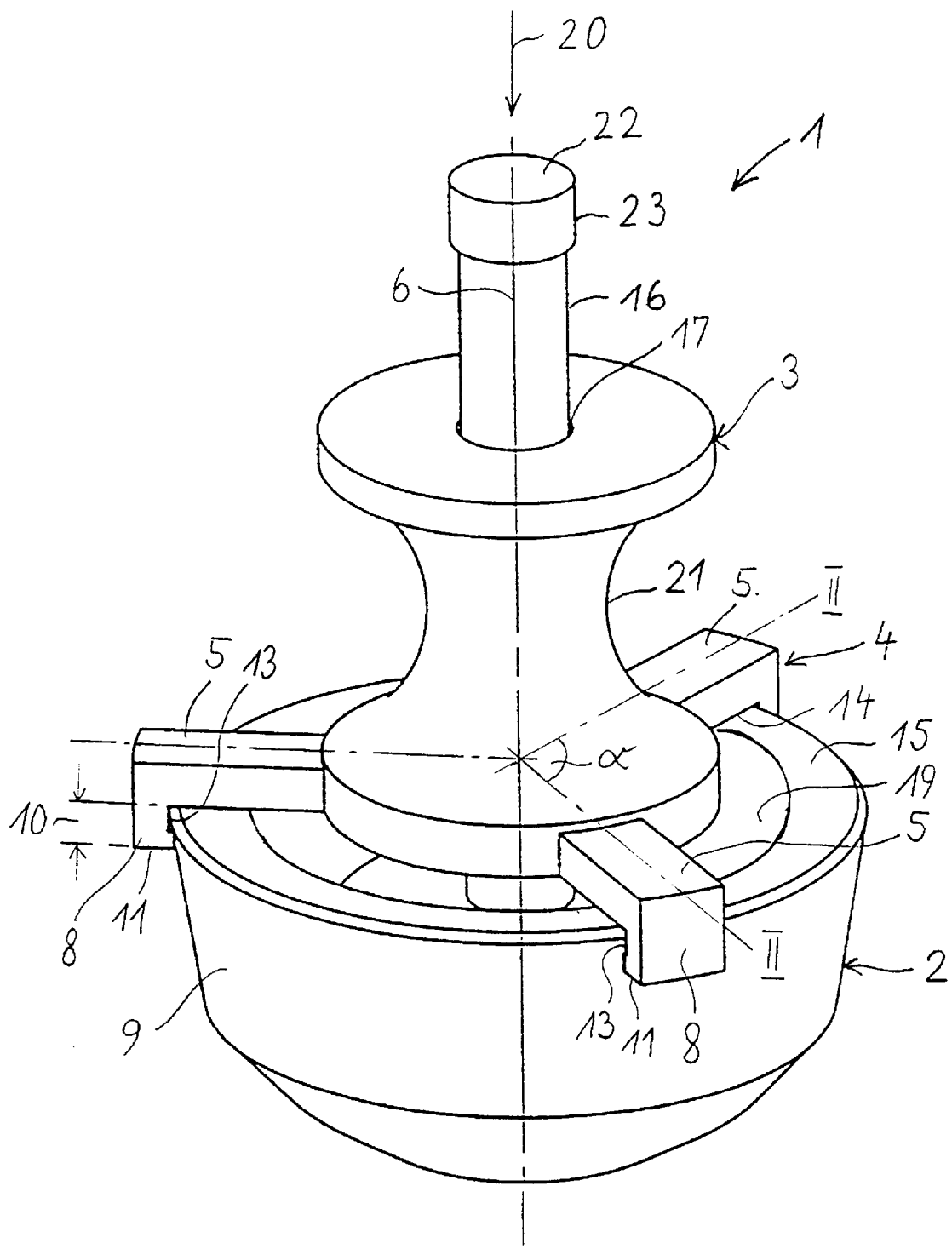
FIG. 1 shows the instrument in accordance with the invention with an insert shell to be inserted in the holding tool.

The representation in the figures is on an enlarged scale. In FIG. 1, 1 denotes the instrument in accordance with the invention for handling and for inserting the insert shell 2 held by it. The instrument 1 comprises a handle 3 and a holding tool 4. In the present exemplifying embodiment, the holding tool 4 has three gripping dogs 5 which extend substantially radially from the longitudinal axis 6 of the handle 3. In the sectional drawing of FIG. 2, this can be seen with the aid of the right angle 7. In the present exemplifying embodiment, the gripping dogs are arranged at equal angular distances →, but this is not absolutely necessary.

Figure 2:
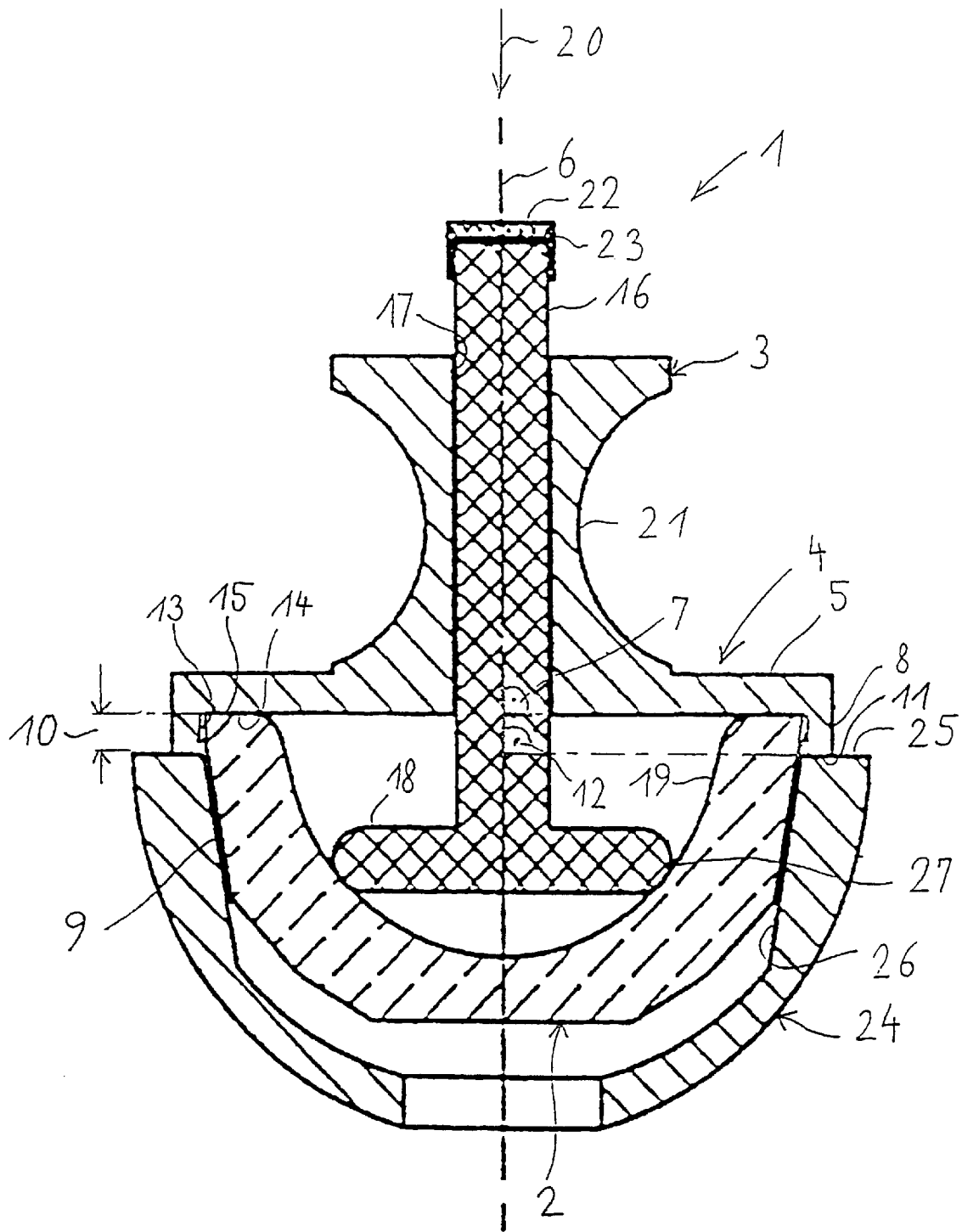
FIG. 2 shows a section along the axis through the handle of the instrument, as drawn in in the Figure.

The gripping dogs 5 have claws 8 which grip over the tapering outer surface 9 of the insert shell 2. In order to take into account the conical shape of the outer surface 9 of the insert shell 2, the claws 8 each have an undercut 13. The claws 8 are all of the same length 10. In order that precise positioning and alignment of the insert shell 2 with respect to the outer shell is possible, the bearing surfaces 14 of the gripping dogs 5, which bearing surfaces rest on the end face 15 of the insert shell 2, are at right angles to the longitudinal axis 6 of the handle 3. Their extension intersects the axis 6 at a right angle 7, as shown in FIG. 2. This renders possible a precise placing of the instrument on to the end face of the outer shell, as is evident from FIG. 2.

In the present exemplifying embodiment, the gripping dogs 5 are elastic, so that when there is a pressure on the insert shell 2 in a direction out of the instrument 1, the claws 8 are bent outwards and release the insert shell 2.

The pushing of the insert shell 2 out of the holding tool 4 takes place by means of a plunger 16. The plunger 16 is mounted in a bore 17 which extends concentrically with respect to the longitudinal axis 6 in the handle 3. In the present exemplifying embodiment, the plunger 16 has a plate 18 at the end which faces the insert shell 2. The outer circumference 27 of this plate rests in a ring-shaped manner on the joint surface 19 of the insert shell 2. The bearing surface lies concentrically with respect to the longitudinal axis 6 of the handle 3, as is evident from FIG. 2. As a result of this, an even introduction of pressing force into the insert shell 2 is ensured. If force is exerted on to the plunger 16 in the direction of the arrow 20, the gripping dogs 5 release the insert shell 2 because of their elasticity.

The handle 3 has a U-shaped recessed grip 21, which extends concentrically around the handle. It is shaped such that the handle can be held, in particular, between two parallel fingers. It is then possible to press on the end face 22 of the plunger 16 with the upper hand or with the thumb, and to push the insert shell 2 out of the holding tool 4. A cap 23 on the end face 22 of the plunger 16 has a diameter which is such that the plunger cannot slide through the bore 17 when the insert shell 2 is pressed into the outer shell. Apart from this, this cap 23 protects the shank 22 in the case of possible blows with a striking tool, and thus prevents chipping or splintering of the forward side edges of the plunger 16.

FIG. 2 shows a longitudinal section through the instrument 1, and the insert shell 2 held by it, in the positioning position on an outer shell 24. The course of the section is indicated by II—II in FIG. 1. It extends through two adjacent gripping dogs 5.

In FIG. 2, the instrument 1, with the insert shell 2 held by it, is placed with the end faces 11 of the claws 8 on the end face 25 of the outer shell 24. The insert shell 2 is positioned in the outer shell 24. Once all of the end faces 11 of the claws 8 have been placed on to the end face 25 of the outer shell 24, precise centring and positioning of the insert shell 2 is ensured.

As is evident from the sectional drawing, the claws 8 grip over the outer surface 9 of the insert shell 2, in the edge region thereof, by the same length 10. This length coincides with the length of the claws 8. The length 10 of the claws 8 is chosen such that when their end faces 11 rest fully on the end face 25 of the outer shell 24, there is still no clamping contact between the outer surface 9 of the insert shell 2 and the inner surface 26 of the outer shell 24.

Not until the plunger 16 is activated by an application of force in the direction of the arrow 20 will the gripping dogs 5 release the insert shell 2 because of their elasticity. In the present exemplifying embodiment, the plunger 16 has, on the end which faces the insert shell 2, a plate 18, the outer circumference 27 of which rests in a ring-shaped manner on the joint surface 19 of the insert shell 2. As a result of an application of force on to the plunger 16 in the direction of the arrow 20, the insert shell 2 is, after release, pressed by the holding tool 4 into the outer shell 24. A press fit takes place because of the conical shapes of the outer surface 9 of the insert shell 2 and of the inner surface 26 of the outer shell 24.

Figure 3:
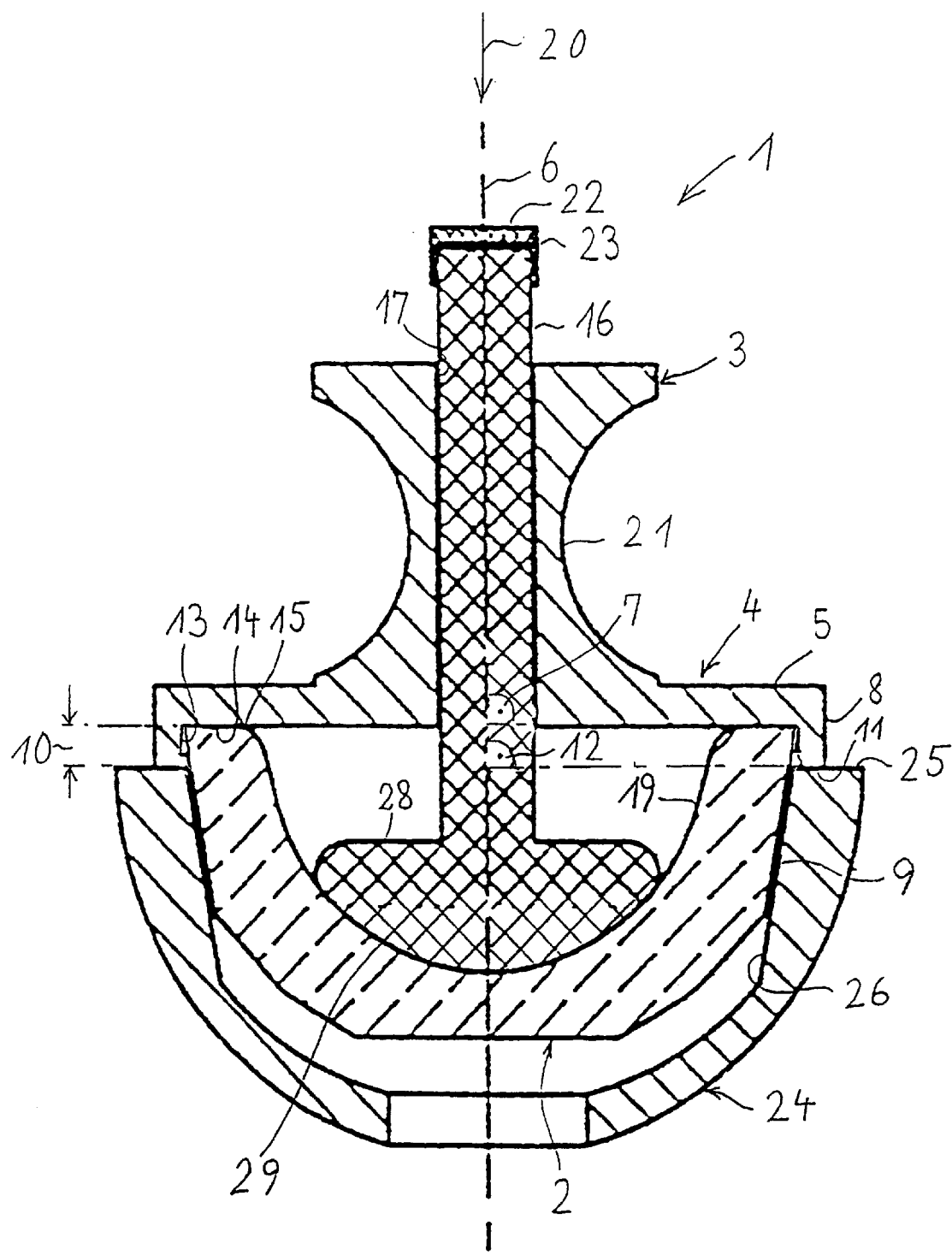
FIG. 3 shows a sectional drawing corresponding to FIG. 2 with a further development of the plunger.

In FIG. 3, which reproduces a sectional drawing corresponding to FIG. 2, the plunger 16 has, on the end which faces the insert shell 2, a stamping head 28 which is matched to the joint surface 19. Features which are the same are provided with the same reference numerals in this exemplifying embodiment. The stamping head 28 has the shape of a spherical segment, and its surface 29 corresponds precisely to that of the joint surface 19 of the insert shell 2. In this embodiment, a large-surface and an even introduction of force onto the insert shell 2 is possible.

The instrument 1 for handling an insert shell 2 can be produced from a sterilisable material, for example from heat-resistant and chemical-resistant plastics, or from a metal having the same properties, so that reuse is possible. The instrument can, however, also be seen as a single-use tool, which is disposed of after use. In this case, it is possible for an insert shell together with an instrument already holding the insert shell with its holding tool, to be made available to the surgeon in sterile packaging. In this way, the manual insertion of the insert shell into the holding tool of the instrument during the operation is dispensed with, which makes the surgeon's operating conditions easier and rules out damage to the sensitive joint surface of the insert shell.

What is claimed is:

1. An instrument for manipulating, detachably holding and placing an insert portion of a joint socket prosthesis into an outer shell of a said prosthesis, said instrument comprising a handle and a holding tool, said holding tool further comprising at least two grasping claws extending substantially radially from the longitudinal axis of said handle, said grasping claws extending over and engaging said insert with said holding tool, and said handle, being elongated and slideably positioned partially within a longitudinal bore in said holding tool, further comprising a plunger distal to said insert, whereby said insert is released when an operator causes said handle to slide within said holding tool towards said insert with sufficient force to disengage said insert from said grasping claws.

2. The instrument of claim 1, wherein said grasping claws further comprise hooks, said hooks having end faces which extend at right angles to the longitudinal axis of said handle, said end faces being capable of radially aligning with and contacting a corresponding face on a circumferential surface of said insert.

3. The instrument of claim 1, wherein said hooks are dimensioned such that when said instrument contacts said corresponding face, a conical outer surface of said insert has no clamping contact with an inner surface of said outer shell.

4. The instrument of claim 1, wherein said grasping claws comprise an elastic material.

5. The instrument of claim 1, wherein said hooks comprise an elastic material.

6. The instrument of claim 1, wherein said handle has a recessed grip.

7. The instrument of claim 6, wherein said recessed grip is U-shaped and circumferential.

8. The instrument of claim 1, wherein the portion of said plunger proximal to said insert further comprises a plate, the outer circumference of said plate capable of being placed on an inside surface of said insert.

9. The instrument of claim 1, wherein the portion of said plunger proximal to said insert further comprises a stamping head having a shape complementary to an inside surface of said insert.

* * * * *